United States Patent [19]

Nason

[11] Patent Number: 5,078,968

[45] Date of Patent: * Jan. 7, 1992

[54] SPECIMEN TEST UNIT

[76] Inventor: Frederic L. Nason, 941 Avenida Acaso, Camarillo, Calif. 93010

[*] Notice: The portion of the term of this patent subsequent to Dec. 18, 2007 has been disclaimed.

[21] Appl. No.: 625,759

[22] Filed: Dec. 10, 1990

Related U.S. Application Data

[63] Continuation of Ser. No. 153,951, Feb. 9, 1988, Pat. No. 4,978,504.

[51] Int. Cl.⁵ .................................................... A61B 10/80
[52] U.S. Cl. .................................................... 422/58; 422/56; 422/61; 422/100; 435/294; 435/295; 128/759; 128/767; 128/771
[58] Field of Search ................... 422/56, 57, 58, 61, 422/101, 102, 100; 435/294, 25, 295, 296, 810; 128/2, 759, 767, 771

[56] References Cited

U.S. PATENT DOCUMENTS

| | | | |
|---|---|---|---|
| 2,490,168 | 2/1947 | Strauss | 128/269 |
| 3,163,160 | 11/1962 | Cohen | 128/2 |
| 3,450,129 | 7/1966 | Avery et al. | 128/2 |
| 3,640,268 | 2/1972 | Davis | 128/2 |
| 3,776,220 | 12/1973 | Monaghan | 128/2 |
| 3,792,699 | 2/1974 | Tobin et al. | 128/2 |
| 3,883,396 | 5/1975 | Thomas et al. | 195/100 |
| 3,890,204 | 7/1975 | Avery | 128/2 |
| 3,913,564 | 10/1975 | Freshley | 128/2 |
| 3,915,806 | 10/1975 | Horlach | 195/139 |
| 3,918,435 | 11/1975 | Beall et al. | 128/2 |
| 3,923,604 | 12/1975 | Monaghan | 128/2 |
| 3,954,563 | 5/1976 | Mennen | 435/810 |
| 3,980,954 | 6/1975 | Greenspan | 128/2 |
| 4,014,746 | 3/1977 | Greenspan | 128/2 |
| 4,014,748 | 3/1977 | Spinner et al. | 128/2 |
| 4,059,404 | 11/1977 | Schuster et al. | 422/56 |
| 4,175,008 | 11/1979 | White | 435/295 |
| 4,184,483 | 1/1980 | Greenspan | 435/295 |
| 4,196,167 | 4/1980 | Olsen | 422/61 |
| 4,223,093 | 9/1980 | Newman et al. | 435/295 |
| 4,300,910 | 11/1981 | Pannwitz | 422/61 |
| 4,311,792 | 1/1982 | Avery | 435/30 |
| 4,312,950 | 1/1982 | Snyder et al. | 435/295 |
| 4,340,670 | 7/1982 | Mennen | 435/25 |
| 4,353,868 | 10/1982 | Joslin et al. | 422/101 |
| 4,355,113 | 10/1982 | Mennen | 422/61 |
| 4,387,725 | 6/1983 | Mull | 128/759 |
| 4,409,988 | 10/1983 | Greenspan | 435/294 |
| 4,562,043 | 12/1985 | Mennen et al. | 435/810 |
| 4,604,360 | 8/1986 | Hounsell | 435/287 |
| 4,635,488 | 1/1987 | Kremer | 422/58 |
| 4,707,450 | 11/1987 | Nason | 422/61 |
| 4,770,853 | 9/1988 | Bernstein | 422/61 |
| 4,903,708 | 2/1990 | Saint-Amand | 422/102 |

FOREIGN PATENT DOCUMENTS

0155747 10/1985 European Pat. Off. .

Primary Examiner—David L. Lacey
Assistant Examiner—Jeffrey R. Snay
Attorney, Agent, or Firm—Kelly, Bauersfeld & Lowry

[57] ABSTRACT

An improved test unit is provided for use in the collection and analysis of biological specimens and the like. The specimen test unit includes a swab member adapted for collection of a specimen to be tested. The test unit incorporates one or more reagents or other test fluids for delivery into contact with the specimen on the swab member. In accordance with various embodiments, the contacted specimen and fluid are then delivered through one or more porous filter members for analysis and/or to contact an additional reagent or reagents in the course of performing a selected test. In some forms, one or more of the porous filter members is preimpregnated with a selected reagent or constituent thereof. Moreover, in some forms, one or more of the porous filter members is formed from a hydrophobic material to serve as a fluid seal until fluid is forced therethrough, for example, by squeezing a reagent-containing housing member of the test unit. In all embodiments, the test unit is substantially self-contained to perform the desired test, with minimal risk of exposing testing personnel to the collected specimen and/or to the various reagents.

36 Claims, 6 Drawing Sheets

SPECIMEN TEST UNIT

BACKGROUND OF THE INVENTION

This application is a continuation of copending application Ser. No. 153,951 filed on Feb. 9, 1988, now U.S. Pat. No. 4,978,504.

This invention relates generally to improvements in medical swabs and the like of the type used for collecting biological specimens for purposes of performing a variety of medical tests with respect to those specimens. More particularly, this invention relates to an improved and substantially self-contained swab unit having one or more reagents and improved means for handling the reagents and the specimen in the course of performing medical tests.

Medical swabs in general are well-known in the art for use in collecting biological specimens from a patient for further analysis. Such medical swabs commonly comprise a fibrous swab tip at one end of an elongated stick or shaft which is manually handled to contact the swab tip with selected tissue cells or other biological specimen obtained, for example, from within the ear, nose or throat of a patient. As a result, some of the targeted biological specimen adheres to the swab tip which can then be contacted with one or more selected reagents to indicate, for example, the presence of infection or other information regarding patient condition. The tests commonly performed with such patient specimens include, by way of example, fluorescent tests, enzymatic tests, monoclonal based tests, agglutination tests, etc.

In accordance with standard techniques, the collected biological specimen is normally transferred from the swab tip to a slide or other laboratory apparatus such as a test tube or the like for contact with the selected reagent and further analysis. However, it is frequently difficult to insure transfer of a sufficient specimen quantity from the swab tip to the laboratory slide or the like to insure accurate test results. Moreover, in many instances, the collected specimen must be transported to a medical laboratory for performance of selected assays, but delays between the time of specimen collection and actual test performance can result in partial or complete drying of the specimen, with a corresponding decrease in test reliability.

Various swab collection devices have been proposed in efforts to provide enhanced contact between a specimen and reagent, or, in the alternative, to sustain the specimen during post-collection transport to a medical laboratory or the like. Such swab collection devices have been provided in the form of a compact kit including a fibrous-tipped swab together with one or more reagents for contacting a specimen collected upon the swab. In some designs, the reagent is carried by a frangible glass ampoule which is broken at the appropriate time to release a reagent for contacting the specimen on the swab tip. Other designs have provided reagents within rupturable plastic cells for appropriate release to contact the collected specimen. These prior collection device designs, however, have not provided effective means for filtering particulate such as mucous and other non-fluid debris from a collected specimen, wherein such filtration of the specimen can be a requirement in order to obtain reliable test results. Moreover, these prior devices have not been designed for relatively easy delivery of a mixed specimen and reagent from the device for further analysis, as required in some test, without exposing testing personnel to unnecessary risks in contacting a collected specimen or the reagents associated therewith.

There exists, therefore, a significant need for an improved specimen test unit having relatively simple yet effective filtering means for filtering the collected specimen and/or reagent, as required by the specific test to be performed. In addition, there exists a need for an improved test unit designed for handling a collected specimen and associated reagents safely without risk of contact by testing personnel. The present invention fulfills these needs and provides further related advantages.

SUMMARY OF THE INVENTION

In accordance with the invention, an improved specimen test unit is provided for use in collecting a biological specimen or the like, for example, from a patient. The invention includes relatively simple and efficient apparatus for applying one or more selected reagents into direct contact with the collected specimen for purposes of performing a selected medical assay. Filter means is provided for filtering reagents and/or the specimen in accordance with the requirements of the test to be conducted.

In accordance with a preferred form of the invention, the specimen test unit comprises an elongated swab member adapted for use in collecting a biological specimen, for example, by directly contacting a portion of the swab member with selected patient tissue, cells, fluids, etc. One end of the swab member is anchored within a porous filter member in the form of a porous plug seated within one end of a generally cylindrical housing member. At least one selected reagent is carried within the housing member, such as within a frangible glass ampoule, wherein the reagent can be released by appropriate bending deformation of the housing member to rupture the ampoule. The released reagent can then be delivered to the swab member by squeezing the housing member sufficiently to force the reagent to flow through the porous plug into contact with the swab member. By appropriate swab member orientation, the reagent flows along the swab member into direct contact with the collected specimen. The porous plug retains the ampoule glass particulate safely within the housing member.

In preferred forms of the invention, the filter plug is preimpregnated with a selected reagent, for example, by presoaking the plug with a reagent and drying that reagent within the plug prior to plug assembly with the housing member. Alternately, multiple porous filter plugs impregnated with different reagents can be mounted end-to-end within the housing member, resulting in serial reagent contact with a selected test fluid forced through the filter plugs upon squeezing of the housing member. Such end-to-end filter plugs are beneficially contoured to insure serial fluid flow therethrough. Moreover, any one of the filter plugs may be constructed with hydrophobic or nonwettable characteristics to define a liquid seal preventing test fluid passage until the test fluid is pressure-forced therethrough by squeezing of the housing member.

In accordance with other preferred aspects of the invention, a cylindrical cap is provided for substantially sealed mounting onto the housing member in a position encasing the swab member, whereby the swab member can be maintained in a sterile package until use. One end of this cylindrical cap may be closed by one or more additional porous filter members, one of which may be formed from a hydrophobic material for normally defining a liquid seal preventing fluid escape from the cap, and further wherein these filter members may be preimpregnated with additional reagents. Accordingly, when the cap is mounted on the housing member, reagent or other test fluid can be expressed from the housing member into contact with a specimen on the swab member, resulting in mixed specimen and test fluid collection within the cap. Further squeezing of the housing member and/or cap is effective to express the mixed specimen and test fluid in drops, for example, onto a laboratory slide or into an auxiliary cartridge which may, if desired, carry still another reagent for contacting the collected specimen. The auxiliary cartridge may include a discharge drop former of conventional construction or, if desired, in the form of another porous filter plug. Alternately, the auxiliary cartridge may incorporate a glass vial or the like into which the mixed specimen and test fluid are delivered for subsequent analysis, for example, by optical detection equipment.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
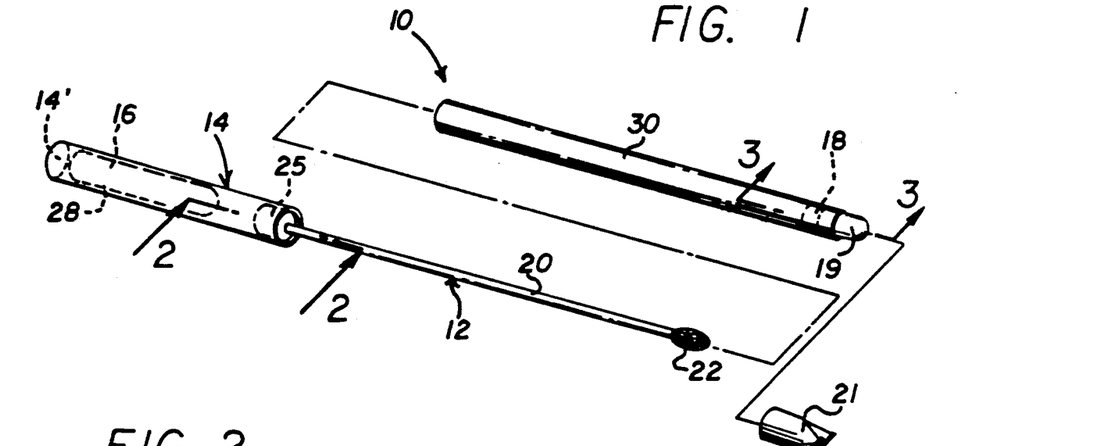
FIG. 1 is an exploded perspective view illustrating one preferred construction for the specimen test unit embodying the novel features of the invention.
Figures 2, 3, 4, 5:
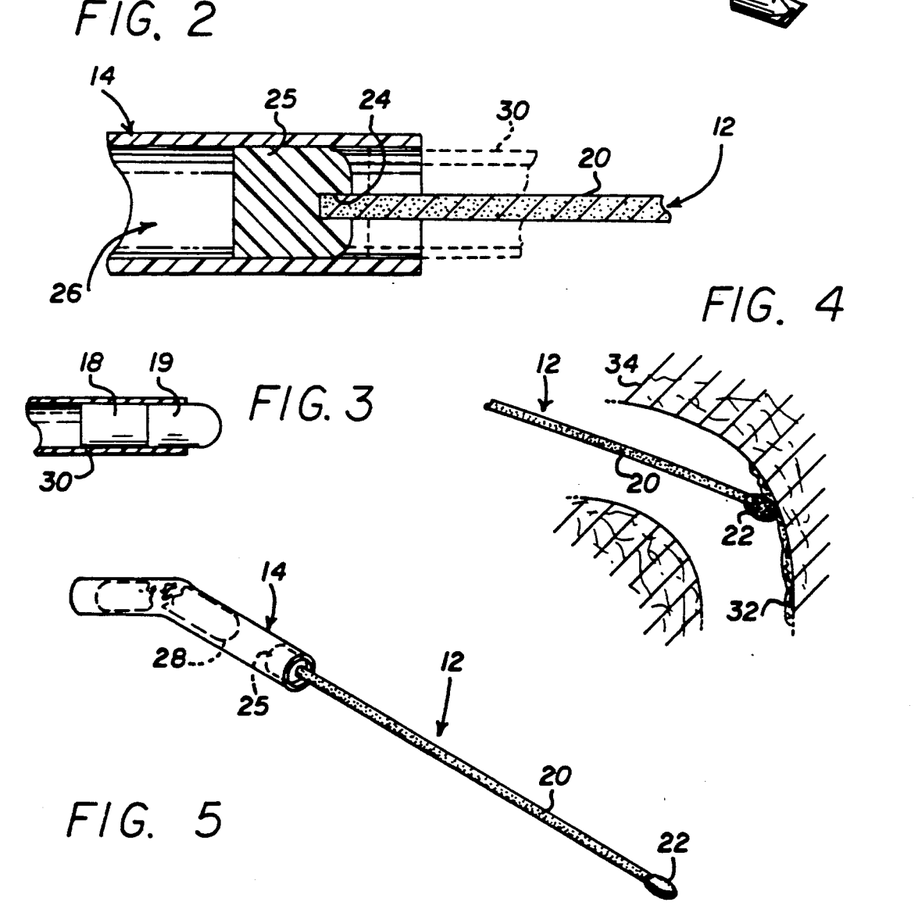
FIG. 2 is an enlarged fragmented sectional view taken generally on the line 2—2 of FIG. 1.
FIG. 3 is an enlarged fragmented vertical sectional view taken generally on the line 3—3 of FIG. 1.
FIG. 4 is a somewhat diagrammatic view illustrating use of the invention in the collection of a biological specimen.
FIG. 5 is a perspective view illustrating a step in releasing a reagent carried by the test unit.
Figure 6:
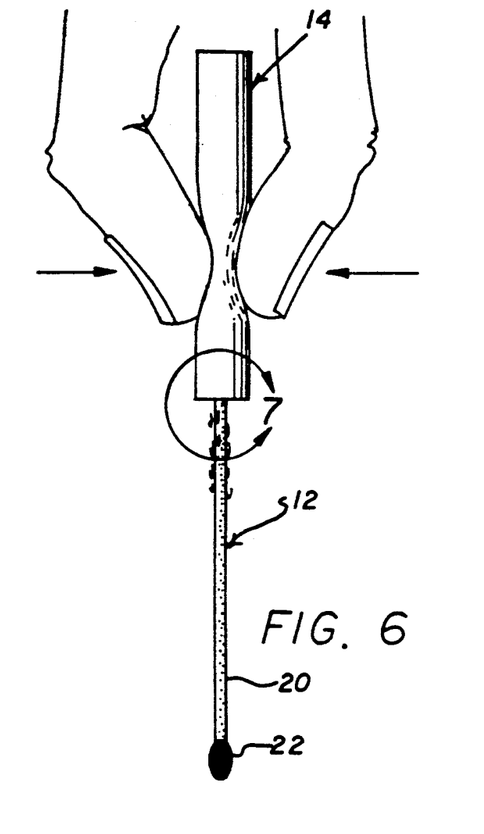
FIG. 6 is an enlarged elevation view depicting filtered transfer of a released reagent to a swab member for direct contact with a collected biological specimen thereon.
Figure 7:
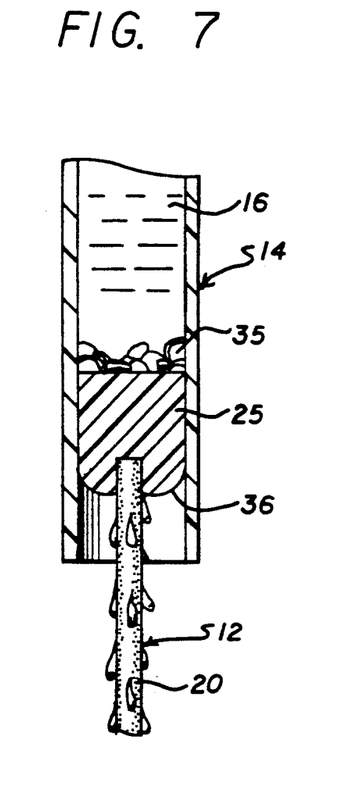
FIG. 7 is an enlarged fragmented vertical sectional view corresponding generally with the encircled region 7 of FIG. 6.

As shown in the exemplary drawings, an improved specimen test unit, referred to generally in FIG. 1 by the reference numeral 10, is provided for use in collecting a biological specimen or the like and for performing a selected test, such as a medical assay, with respect to the collected specimen. The test unit 10 comprises the combination of a swab member 12 projecting from an enlarged housing member or base 14 having one or more reagents 16 or other test fluid encased therein. At least one filter member such as a pair of filter members 18 and 19 are incorporated into the test unit 10 for filtering the reagent and/or the specimen as required for the selected test, and in a manner to be described in more detail herein.

The improved specimen test unit 10 of the present invention provides a relatively simple and self-contained product for collecting and testing biological specimens such as tissue, cells, body fluid, and the like obtained from a patient. The test unit provides means for substantial and thorough contact of the collected specimen with one or more selected reagents, without requiring additional test apparatus such as laboratory slides, test tubes, etc. A wide variety of selected tests may be performed and the results read directly at a selected location within the test unit, after which the entire test unit may discarded as a disposable item. Alternately, the specimen and associated test fluid can be delivered safely and efficiently from the test unit 10 for further laboratory analysis or the like, without exposing test personnel or others to unnecessary exposure to the specimen or associated reagents. Importantly, the test unit 10 incorporates relatively simple yet highly effective filter means to provide appropriate fluid filtering at various stages within the test unit, as required by the particular test to be performed. Examples of tests in which the test unit 10 may be used include, but are not limited to, fluorescent tests, enzymatic tests, monoclonal based tests, agglutination tests, and the like.

As shown in detail in FIGS. 1-7, with respect to one preferred form of the invention, the specimen test unit 10 constitutes an elongated, relatively thin implement having an overall size and shape for easy manual handling during use. More specifically, the test unit 10 comprises the swab member 12 shown in FIG. 1 in the form of an elongated shank or shaft 20 supporting a swab tip 22 of cotton, Dacron or other absorbent fibrous material which is wound or otherwise suitably attached to the forward end of the shank 20. The shank 20 is formed from a plastic or other suitable material to have a relatively stiff but somewhat flexible construction corresponding generally with the construction of conventional swabs used in the medical environment.

The rear end of the swab shank 20 is seated within a shallow counterbore 24 formed in a porous filter member or plug 25, wherein the filter member is mounted in turn within the housing member 14 for the test unit 10. As shown best in FIGS. 1 and 2, the housing member 14 has a generally cylindrical hollow construction with a closed rear end wall 14' and an open front end for relatively snug-fit slide-in reception of the filter member 25. The filter member 25 cooperates with the housing member 14 to define a substantially closed reagent chamber 26 for containing at least one reagent, such as the reagent 16 encased initially within a frangible glass ampoule 28.

A cylindrical cap 30 is provided as part of the specimen test unit 10 and has a rearwardly open construction to fit over the swab member 12 in seated relation extending partially into the open front end of the housing member 14. In this closed configuration, the cap 30 covers and protects the swab member 12, including the shank 20 and the swab tip 22, thereby permitting the test unit 10 to be supplied with the swab 12 initially in a closed sterile condition. In this regard, the filter member 25 is slightly inset into the front end of the housing member 14 (FIG. 2) to accommodate slide-in reception of the cap rear end. Alternately, the cap rear end can be sized for sliding fit over the front end of the housing member 14.

When performance of a medical test is desired, the cap 30 is removed quickly and easily from the housing member 14 to expose the swab member 12 for use in collecting the medical specimen. More specifically, as shown generally in FIG. 4, the test unit 10 can be manually handled to move the swab tip 22 into contact with and to collect tissues or cells or other biological materials 32 which may be present, for example, within the throat 34 of a patient. Alternately, a wide variety of other types of biological or other specimens may be collected in accordance with the tests or analyses to be performed. Conveniently, the swab shank 20 is normally provided with sufficient bending capability to accommodate specimen collection while also providing sufficient rigidity to permit the swab tip 22 to be pressed or scraped against the tissues or cells during specimen collection.

Once the specimen has been collected on the swab tip 22, the cylindrical housing member 14 of the test unit 10 can be bent or squeezed or otherwise deformed to fracture the reagent-containing ampoule 28 within the reagent chamber 26. To this end, the housing member 14 is constructed from a plastic or the like having sufficient flexibility to accommodate this deformation and then return elastically substantially to the initial nondeformed state. When the ampoule 28 is fractured, as viewed in FIG. 5, the reagent 16 therein is released for delivery to the collected specimen at the swab tip 22. This delivery is achieved by manually pressing the side walls of the housing member 14, as viewed in FIG. 6, to increase the pressure within the reagent chamber 26 sufficiently to drive or force the liquid reagent through the open porous structure of the filter member 25, as viewed in FIGS. 6 and 7. During this reagent delivery step, the test unit 10 is normally oriented in a substantially vertical position causing the reagent to drain downwardly along the shank 20 into direct contact with the swab tip 22 and the specimen collected thereon.

The porous filter member 25 advantageously separates the reagent 16 from glass particles and fragments 35 (FIG. 7) remaining within the housing member 14 upon ampoule fracture. Accordingly, the glass particles and fragments 35 do not drain along the swab shank 20 and do not contact the swab tip 22, whereby the glass fragments do not interfere with performance of the selected test and do not pose a safety hazard. In this regard, the preferred filter member 25 is formed as a molded plastic filter plug material such as a blown polyethylene plastic or resin or the like having a controlled porosity typically for filtering particles to a size within the range of about 3 to about 10 microns. Such filter plugs are commercially available, for example, from Porex Technologies of Fairburn, Va., or from Chromex Corporation of Brooklyn, N.Y. In addition, to insure reagent flow onto the swab shank 20 for drainage to the swab tip 22, when the test unit 10 is vertically oriented as viewed in FIGS. 6 and 7, the front nose 36 of the plug 25 is rounded (FIG. 7) to define a generally outwardly presented convex surface which guides reagent flow onto the shank 20. This step of delivering the reagent to the swab tip 22 is normally performed with the cylindrical cap 30 held loosely about the swab member 12, whereby the cap 30 can be used to collect excess reagent dripping from the swab tip 22.

In accordance with various specific test applications, the ampoule 28 within the housing member 14 may contain a wetting solution such as water, saline solution, etc., in accordance with the requirements of the selected test. In this instance, the filter member 25 can be preimpregnated with a selected reagent, for example, by presoaking the plug 25 with a selected reagent which is allowed to dry prior to plug installation into the housing member 14. Subsequent delivery of the wetting agent through the plug 25 returns the dried reagent to solution form for transfer along the swab shank 20 to the swab tip, in the same manner as previously described.

Figure 8:
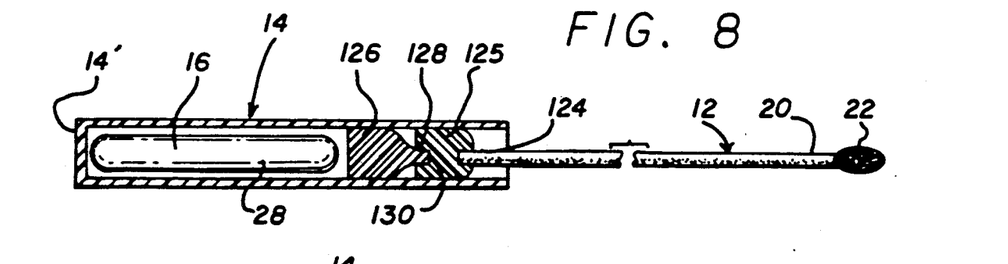
FIG. 8 is a fragmented longitudinal sectional view illustrating one alternative preferred form of the invention.

Several alternative embodiments of the swab member of the test unit are shown generally in FIGS. 8-11, wherein components identical to those depicted in FIGS. 1-7 are referred to by the same reference numerals. More particularly, as shown in FIG. 8, a cylindrical housing member 14 contains a reagent 16 within a frangible ampoule 28 or the like, but in this embodiment, multiple filter members 125 and 126 are provided for series passage of the reagent 16 or other test fluid within the housing member 14. More particularly, a first filter member 125 is received into the front end of the housing member 14 and includes a shallow front counterbore 124 for seated reception of the shank 20 of the swab member 12. However, this first filter member 125 additionally has a shallow counterbore 128 in the rear face thereof for snap-fit reception or the like of a tapered nose 130 of the second filter member 126. Both of these filter members 125 and 126 can be preimpregnated with different reagents for series contact with the reagent 16 or other test fluid when that test fluid is expressed from the housing member. Moreover, the second filter member 126 can be formed from a sufficiently hydrophobic material to provide an effective liquid seal unless and until the housing member is squeezed to express the reagent 16. Conveniently, the contoured or tapered nose 130 of the second filter member 126 assures test fluid passage serially through the first member 125, rather than by leakage around the first filter member 125. Moreover, both filter members 125 and 126 may be conveniently constructed as porous filter plugs similar to the filter plug 25 shown in FIGS. 1–7.

Figure 9:
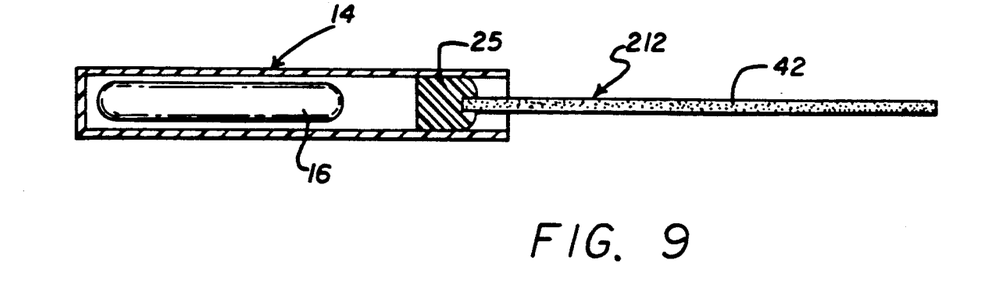
FIG. 9 is a longitudinal sectional view illustrating another alternative preferred form of the invention.

In the embodiment shown in FIG. 9, a simplified swab member 212 is shown in the form of an absorbent rod 42 projecting forwardly from the porous filter member 25 at the front end of a housing member 14. In this version, the absorbent rod 42 can be used to collect a specimen thereon at any convenient position along the length of the rod, after which the reagent 16 or other test fluid can be expressed to the rod in the same manner as previously described. However, the reagent not only drains along the rod but also wicks thereinto for purposes of contacting the collected specimen. Of course, if desired, one or more filter members having reagents preimpregnated therein may be used, with multiple filter members being adapted for serial test fluid passage, as viewed in FIG. 8.

Figure 10:
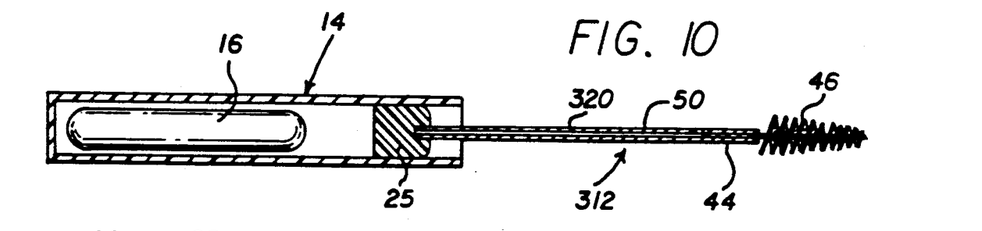
FIG. 10 is a longitudinal sectional view depicting still another alternative preferred form of the invention.

A further alternative embodiment of the invention is shown in FIG. 10, wherein a further modified swab member 312 includes a hollow swab shank 320 having a rear end anchored into the porous filter member 25. In this version, the forward end of the swab shank 320 receives a short mounting stem 44 of a brush 46 having bristles for collection of the desired specimen. The reagent 16 is expressed through the filter member 25 for flow through and about the swab shank 320 into contact with the brush bristles, in generally the same manner as previously described with respect to FIGS. 1–7. However, reagent flowing through the swab shank interior is permitted to discharge therefrom through a small port 50 near the shank front end for subsequent flow to the brush bristles 46. Multiple filter members adapted for serial test fluid passage may again be provided, if desired.

Figure 11:
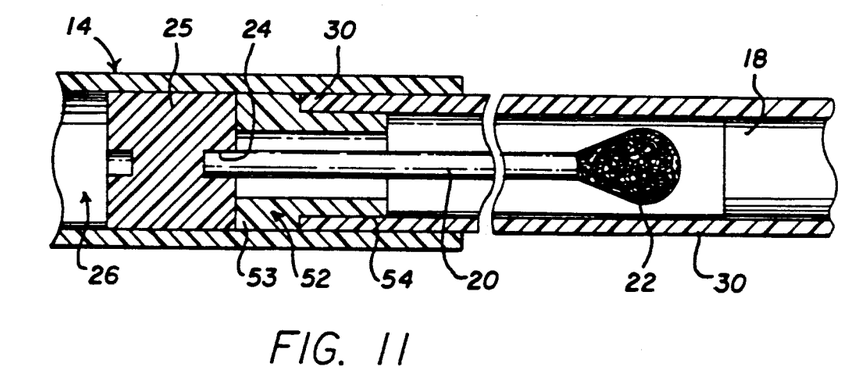
FIG. 11 is an enlarged fragmented sectional view showing a further alternative construction for the invention, including a sealing cap for use in combination with the test unit.

FIG. 11 illustrates still another alternative configuration of the invention to include a cap seal ring 52 within the housing member 14 for sealing engagement with the cap 30, thereby insuring sterility of the product prior to use. In this embodiment, the housing member 14 again has an open front end for snug, slide-fit reception of the porous filter member 25 having the shallow counterbore 24 in the front face or nose thereof to receive and anchor the rear end of the swab member 12. Of course, any of the various swab members shown in FIGS. 1–7 can be used. The seal ring 52 is also seated into the front end of the housing member 14 and includes a cylindrical base 53 abutting against the forwardmost face of the filter member 25. This base 53 is received tightly into the housing member 14 and is joined to a forwardly projecting annular lip 54 of reduced diametric size. The lip 54 cooperates with the interior surface of the housing member 14 to define a forwardly open annular recess for snug, substantially sealed reception of the rearmost edge of the cylindrical cap 30. Accordingly, the seal ring 52 and the cap 30 cooperate to define a high quality seal maintaining the sterility of the swab member 12 at least until the cap is removed.

Figures 12, 14, 15, 16:
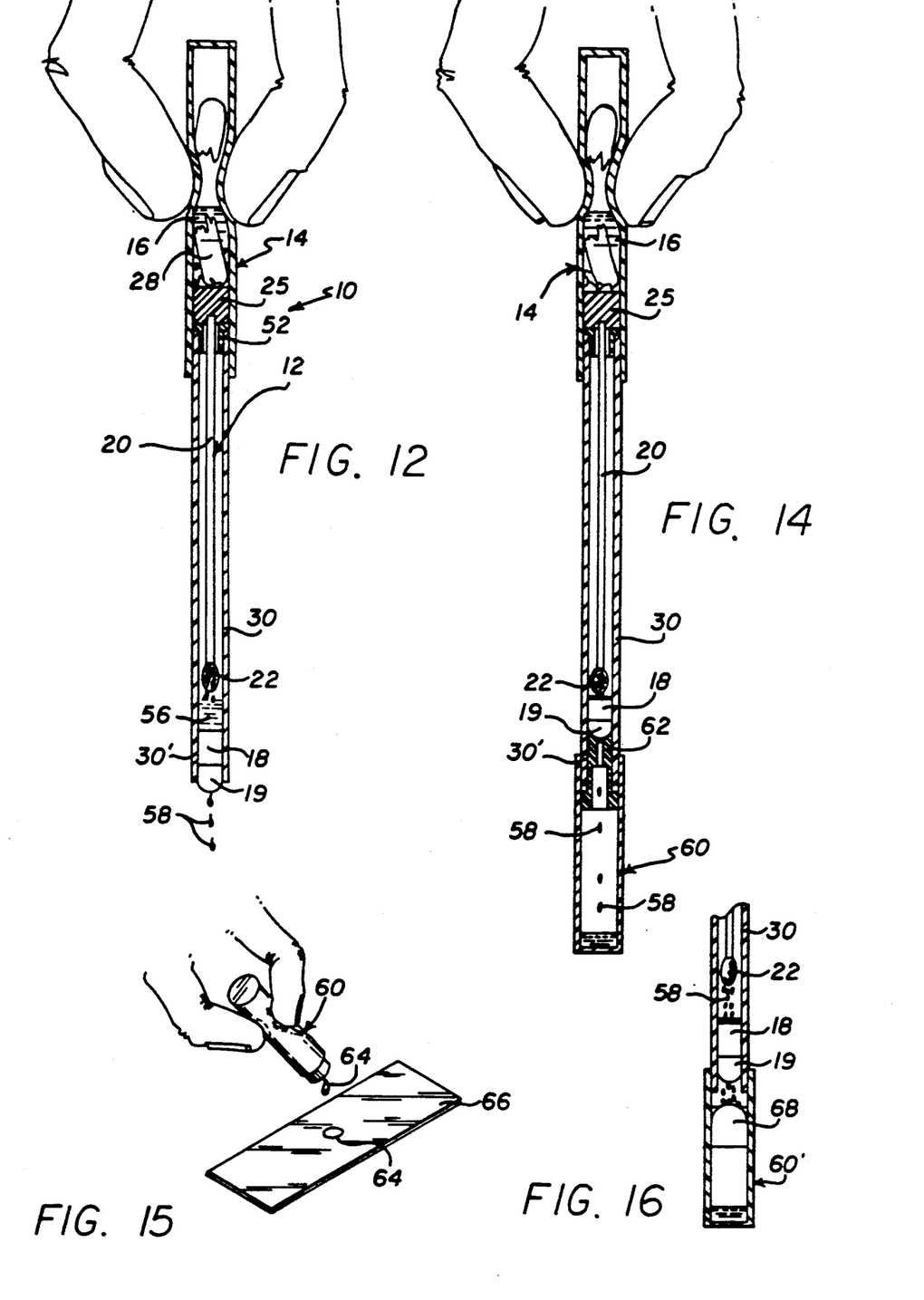
FIG. 12 is a vertical sectional view showing use of the embodiment of FIG. 11.
FIG. 14 is an enlarged fragmented sectional view illustrating use of the embodiment of FIG. 13.
FIG. 15 is a perspective view showing expression of fluid from the auxiliary dropper cartridge.
FIG. 16 is a fragmented sectional view illustrating an alternative configuration for the auxiliary dropper cartridge.

Regardless of the particular selected configuration of the swab member, as described in FIGS. 1-11, the collected specimen is contacted by and mixed with the test fluid including the reagent or reagents for form a liquid pool 56 at the bottom of the cylindrical cap 30, as viewed in FIG. 12. Importantly, the lower or outboard end 30' of the cylindrical cap 30 is closed by at least one additional porous filter member, such as the serially mounted pair of filter members 18 and 19 shown in the drawings. A small end cap 21 (FIG. 1) is also normally provided to enclose the filter members 18 and 19 prior to use of the test unit. The lowermost filter member 19 protrudes a short distance from the cap 30 and terminates in a rounded contour, such as the hemispherical contour shown in the drawings. Both filter plugs 18 and 19 may, if desired, be preimpregnated with selected reagents, and one or both of the filter plugs 18 and 19 may have hydrophobic characteristics to define a fluid seal which normally prevents fluid leakage from the within the cap 30.

The mixed specimen and reagent pool 56 within the cap 30 can be expressed through the filter members 18 and 19 for performance of further tests. More particularly, as viewed in FIG. 12, the cap 30 can be resecured onto the housing member 14 with its upper or open end in substantially sealed relation with the housing member. In this configuration, the housing member 14 and/or the cap 30 can be squeezed again to express the mixed reagent and specimen 56 through the filter plugs 18 and 19. Such expression of the fluid beneficially filters the specimen and/or reagent, and further functions to contact the specimen with any additional reagents carried by the filter members 18 and 19. The rounded front contour of the filter plug 19 advantageously insures formation of discrete droplets 58 of mixed reagent and specimen which can be subjected to further testing, for example, by placement onto a slide or the like (not shown in FIG. 12) for further laboratory analysis.

Figure 13:
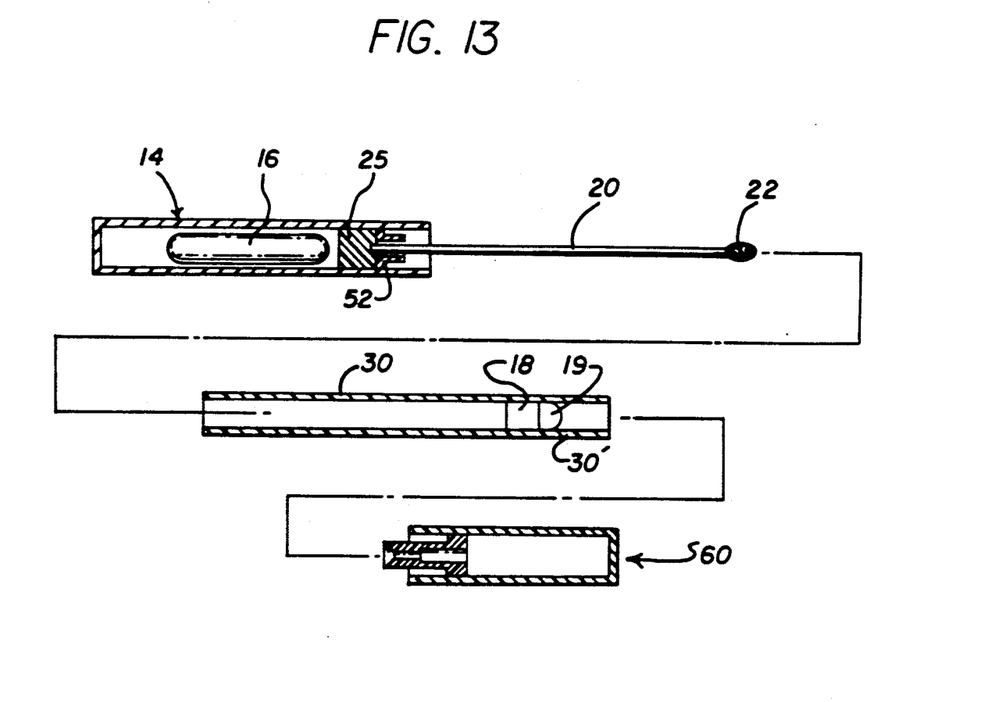
FIG. 13 is an exploded sectional view showing the test unit for use in combination with a further modified sealing cap and auxiliary dropper cartridge.

The invention can be adapted for use with an auxiliary droplet cartridge 60 by insetting the filter plugs 18 and 19 a short distance from the outboard end 30' of the cap 30, as viewed in FIGS. 13 and 14. This permits the cap outboard end 30' to seat snugly and in substantially sealed relation into the open end of the cylindrical cartridge 60 having a drop former 62 on conventional design received therein. Still another reagent may be placed within the cartridge 60, if desired. The thus-modified unit can then be used to express the droplets 58 through the filter plugs 18 and 19 and further through the drop former 62 for mixture with the reagent in the cartridge 60. The mixed specimen and reagents can then be expressed in turn from the cartridge 60 in discrete droplets 64 onto a slide 66 or the like for further analysis, as shown in FIG. 15. Alternately, a modified cartridge 60' may include another porous filter member or plug 68 as the drop former structure, as viewed in FIG. 16.

Figures 17, 18, 19:
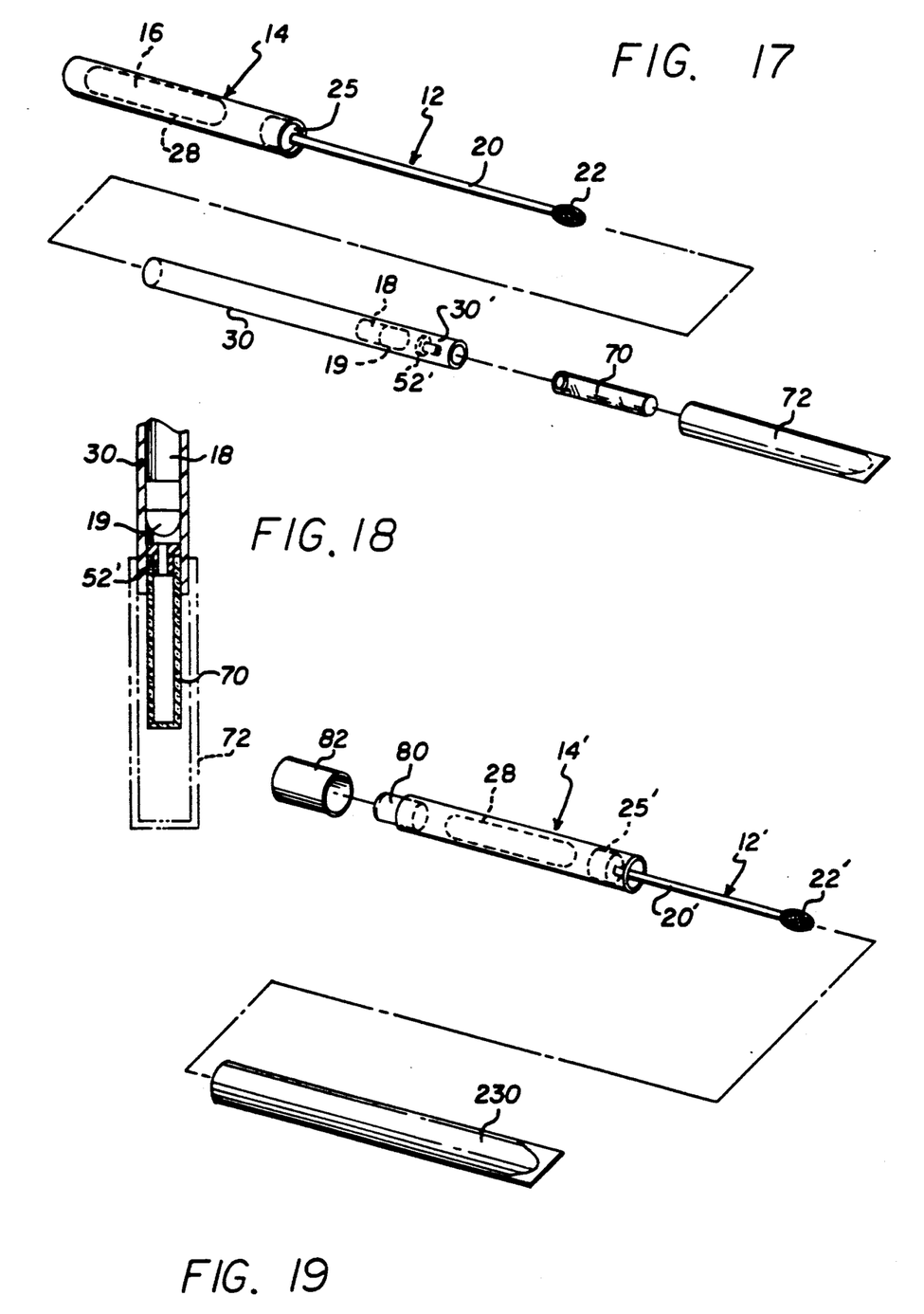
FIG. 17 is an exploded perspective view showing another alternative construction of a specimen test unit formed in accordance with the invention.
FIG. 18 is an enlarged fragmented vertical sectional view of a portion of the embodiment of FIG. 17 to depict use thereof in handling and processing a collected biological specimen.
FIG. 19 is another exploded perspective view showing still another alternative configuration of the invention.

A further modified form of the invention is shown in FIGS. 17 and 18, wherein components identical to previously described embodiments are again designated by the same reference numerals. In this version, the housing member 14 again contains a reagent 16 or other test fluid within a rupturable ampoule 28 for expressed delivery through a porous filter member 25 to a swab member 12 or the like having, for example, a shank 20 and absorbent tip 22. A cylindrical cap 30 of open-ended construction is provided for mounting onto the housing member 14 to cover and protect the swab member 12, and includes an outboard end 30, with one or more axially inset porous filter members, such as the illustrative plugs 18 and 19.

As shown best in FIG. 18, the outboard end 30' of the cap 30 also carries a small seal ring 52' which may be similar in construction to the seal ring 52 shown and described with respect to FIG. 11. The seal ring 52', however, is adapted for normal sealed engagement and friction fit with the open upper end of a small glass vial 70 or the like. An outer end cap 72 is normally provided for mounting onto the outboard end 30' of the cap 30 to cover and protect the glass vial 70. In normal construction, the end cap 72 and the cap 30 will be formed from plastic material.

In use of the embodiment of FIGS. 17 and 18, a specimen will be collected as previously described herein and then contacted with one or more reagents by appropriate delivery of the test fluid 16 from the housing member 14 to contact the swab tip 22. The mixed specimen and reagent can then be delivered from the cap 30 by expression through the filter members 18 and 19, again as previously described. In this version, however, the mixed specimen and reagent are delivered into the glass vial 70. The glass vial 70 can then be placed into an appropriate optical detection device or the like for reading, for example, selected parameters of the mixed specimen/test fluid such as turbidity, color, etc. Importantly, the glass vial 70 can be placed into the optical detection device without requiring the vial to be touched by human hands, by removing the end cap 72 and placing the remainder of the test unit into an examination station of the optical detection device. This procedure advantageously isolates the vial from fingerprints, etc., which could adversely affect test read-out, and also safeguards against human contact with the specimen and reagents. Alternately, if desired, the glass vial can be separated from the cap 30 by squeezing inwardly on the end cap 72 to grasp and remove both components simultaneously from the cap 30.

A further modified form of the invention is shown in FIGS. 19-22, wherein this form of the invention is designed to express mixed specimen and reagent from the end of a housing member 14' opposite a supported swab member 12'. More specifically, with reference to FIG. 19, the modified housing member 14' is open-ended in construction with a hollow support member 25' at one end cooperating with a porous filter member 80 at the opposite end to retain a reagent containing ampoule 28 or the like within the housing member. A hollow tube swab shank 20' has an upper end communicating through the support member 25' and a lower end carrying a porous, absorbent tip 22'. An elongated cap 230 is adapted to fit with one end of the housing member 14' over the swab member 12', and shorter end cap 82 is adapted to fit over the porous filter member 80 at the other end of the housing member.

Figures 20, 21, 22:
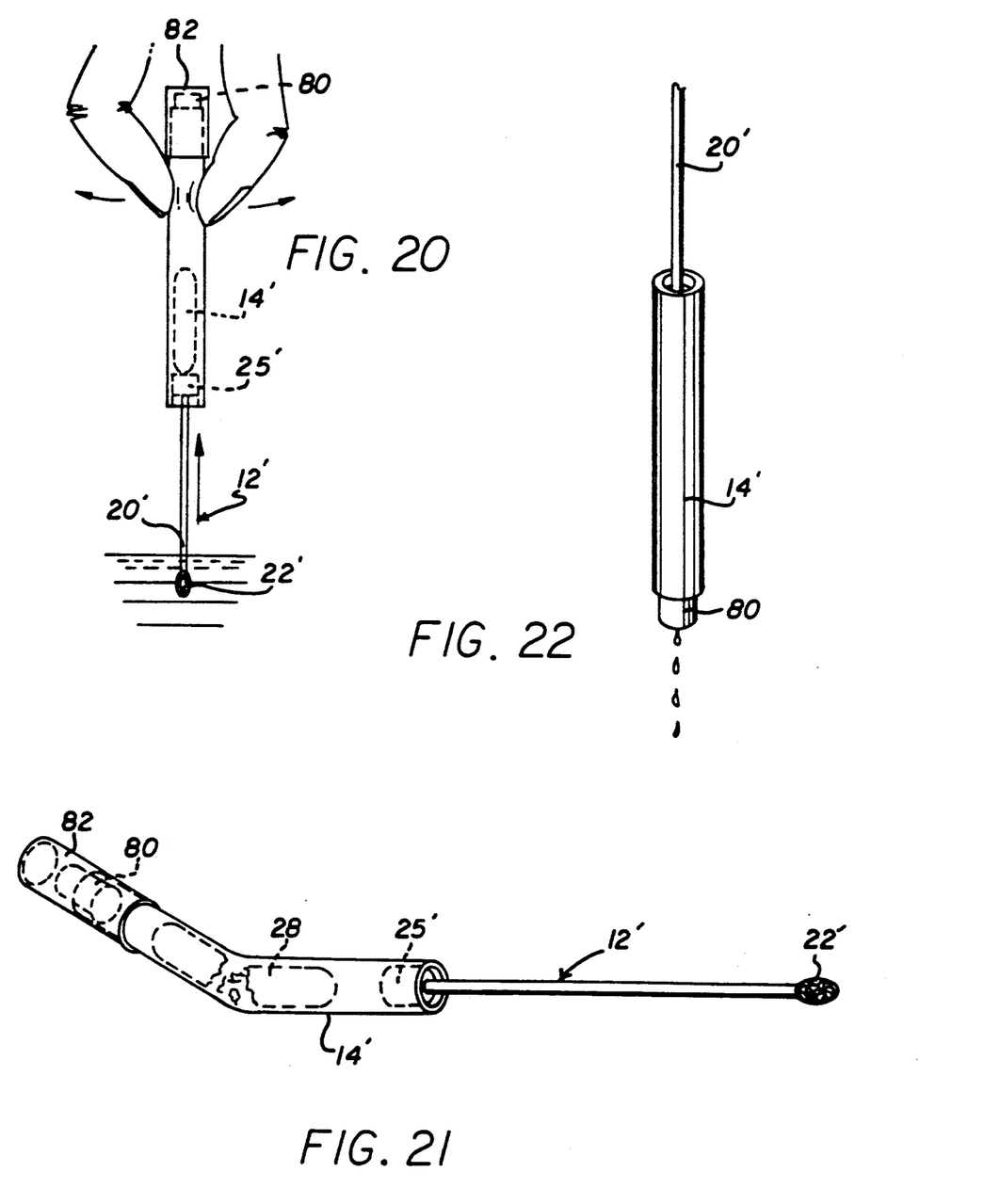
FIG. 20 is a side elevation view showing use of the embodiment of FIG. 19 for drawing a liquid or liquid-containing specimen for test purposes.
FIG. 21 is a perspective view illustrating release of a reagent for contacting the collected specimen, using the embodiment of FIG. 19.
FIG. 22 is a perspective view illustrating delivery of a collected specimen and reagent from the embodiment of FIG. 19.

In use, the elongated cap 230 is removed from the swab member 12' to permit a liquid specimen or liquid-carried specimen to be drawn by suction through the swab shank 20' into the interior of the housing member 14'. During this drawing step, as viewed in FIG. 20, the flexible plastic walls of the housing member 14' are first squeezed inwardly and then released to draw the specimen, with the specimen initially passing through the swab tip 22' for filtering purposes. The ampoule 28 can then be ruptured to release the reagent therein, as viewed in FIG. 21, followed by inversion of the housing member 14' to permit expression of the mixed specimen and reagent therein through the porous filter member 80, as shown in FIG. 22, upon appropriate inward squeezing of the side walls of the housing member 14'.

The specimen test unit of the present invention thus provides a variety of different configurations each incorporating one or more porous filter members through which liquid specimen and/or reagents or the like may be expressed. The filter members provide simple yet highly effective means for filtering particulate matter from reagents and/or from a specimen, as required by the test to be performed. In any one of the various embodiments, the filter member or members may be preimpregnated with a selected reagent. The test results can be read directly, for example, by observing colormetric changes or the like at various locations such as on any one of the filter members or the swab member, or by depositing mixed reagent and specimen onto a slide or the like for further analysis.

As one illustrative example of use of the invention, direct antigen testing can be performed quickly and easily, and in a manner which minimizes opportunity of exposure of testing personnel to the targeted organism and/or to the reagents used. One such direct antigen test in known for detecting Strep A, wherein the swab member can be used to collect a specimen which is then contacted with an appropriate succession of reagents and filtered to yield a colormetric indication located, for example, on a surface of one of the porous filter members. Of course, a wide range of different tests may be performed, with the invention providing a highly convenient, self-contained kit for safe specimen handling and prolonged storage of the appropriate reagents.

A variety of further modifications and improvements to the specimen test unit will be apparent to those skilled in the art. For example, in one form, the porous filter member can be formed simultaneously and integrally with the encasing housing member or the like, with the filter member having blown characteristics including the desired porous construction not present in the housing member. Accordingly, no limitation on the invention is intended by way of the description herein and the accompanying drawings, except as set forth in the appended claims.

What is claimed is:

1. A specimen test unit for use in collection and analysis of a biological specimen, said test unit comprising:

a housing defining a specimen chamber and having at least one test fluid therein, said housing including first and second separable and interfitting housing members which cooperatively define said specimen chamber;

specimen collecting means for collecting the specimen;

said first and second housing members and said collecting means being arranged so that said specimen collecting means and the specimen collected thereby can be placed into said specimen chamber and the collected specimen can be selectively contacted with said at least one test fluid within said specimen chamber; and said first housing member having an outlet port formed therein, means for preventing fluid passage through said outlet port during contacting of the collected specimen with said at least one test fluid within said specimen chamber, and said housing further including delivering means for delivering at least a portion of the collected specimen and test fluid contacted therewith from said specimen chamber through said outlet port to the exterior of said housing for analysis, said delivering means comprising a deformable portion of said housing to permit said housing to be deformed to increase the relative pressure within said specimen chamber to deliver at least a portion of the collected specimen and test fluid through said outlet port.

2. The specimen test unit of claim 1 wherein said at least one test fluid is carried within a frangible ampoule disposed within said housing.

3. The specimen test unit of claim 1 wherein said specimen collecting means comprises a swab member carried by said housing.

4. The specimen test unit of claim 1 wherein said test fluid comprises a reagent.

5. The specimen test unit of claim 1 further including a glass vial positioned and arranged for mounting onto said first housing member so as to to receive the specimen and test fluid from said specimen chamber, and a protective cover positioned and arranged so as to engage with said first housing member in overlying relation with said glass vial.

6. The specimen test unit of claim 1 wherein said means for preventing fluid passage through said outlet port comprises a cap removably mounted on said first housing member.

7. The specimen test unit of claim 6 further including a filter seated within and substantially closing said outlet port.

8. The specimen test unit of claim 1 wherein said specimen collecting means comprises a swab member which includes a shank having a swab tip at one end thereof for collecting the specimen.

9. The specimen test unit of claim 8 wherein said swab tip comprises an absorbent material.

10. The specimen test unit of claim 8 wherein said swab tip comprises a brush having bristles.

11. The specimen test unit of claim 8 wherein said swab member comprises an absorbent rod having one end supported by said second housing member.

12. The specimen test unit of claim 1 further including a dropper unit positioned and arranged for mounting onto said first housing member in a position so as to cover said outlet port, said dropper unit including means for receiving the specimen and test fluid from said specimen chamber and for expressing fluids in drops from said dropper unit.

13. The specimen test unit of claim 12 wherein said dropper unit includes an additional porous filter member.

14. The specimen test unit of claim 12 further including an additional reagent within said dropper unit.

15. The specimen test unit of claim 1 wherein sid second housing member further defines a test fluid chamber having said at least one test fluid therein, and test fluid delivering means for delivering said at least one test fluid from said test fluid chamber to said specimen chamber for contacting the specimen within said specimen chamber, said test fluid delivering means comprising a sufficiently deformable material defining said second housing member to permit said second housing member to be squeezed to increase the pressure within sid test fluid chamber, and passage means for permitting flow of said at least one test fluid from said test fluid chamber to said specimen chamber when said second housing member is squeezed.

16. The specimen test unit of claim 15 wherein said passage means comprises a porous filter member.

17. The specimen test unit of claim 16 wherein said porous filter member is pre-impregnated with a selected reagent.

18. The specimen test unit of claim 16 wherein said at least one test fluid is contained within a rupturable ampoule within said test fluid chamber, said second housing member being deformable sufficiently to rupture said ampoule to release said test fluid, said filter member constructed so as to permit passage of said test fluid b ut confining said ampoule to said test fluid chamber.

19. The specimen test unit of claim 16 wherein said filter member comprises a porous plug having an open pore size in the range of about 3 to about 10 microns.

20. The specimen test unit of claim 16 wherein said filter member comprises a plastic filter plug.

21. The specimen test unit of claim 17 wherein said test fluid is a fluid that will solubilize said reagent carried by said filter member upon passage of said test fluid through said filter member.

22. The specimen test unit of claim 1 wherein said means for preventing fluid passage through said outlet port comprises a filter seated within and substantially closing said outlet port.

23. The specimen test unit of claim 22 wherein said means for preventing fluid passage through said outlet port further comprises a cap.

24. The specimen test unit of claim 23 further including seal means cooperating between said second housing member and said cap to maintain a substantially sterile seal therebetween.

25. The specimen test unit of claim 23 wherein said filter comprises at least one porous filter member supported by said cap, at least one said first and second housing members being squeezable while interfitted to force the specimen from said specimen chamber through said filter.

26. The specimen test unit of claim 25 wherein said filter member includes a rounded nose projecting outwardly from said cap.

27. The specimen test unit of claim 25 wherein said at least one filter member is formed from a hydrophobic material to provide a substantial fluid seal.

28. The specimen test unit of claim 25 wherein said at least one filter member comprises at least two of said filter members disposed for series passage of the collected specimen, at least one of said filter members having a reagent pre-impregnated therein.

29. The specimen test unit of claim 28 wherein said at least two filter members have different reagents pre-impregnated therein.

30. A specimen test unit for use in collection and analysis of a biological specimen, said test unit comprising:

a housing defined by first and second separable and intefitting housing members, said second housing member including means defining a test fluid chamber having at least one test fluid therein, and said first and second housing members including cooperative means which interfit so as to define a specimen chamber;

means for collecting a specimen and for placement with the collected specimen into the specimen chamber;

said housing further including means for delivering said test fluid from said test fluid chamber to said specimen chamber for contacting the collected specimen placed into said specimen chamber, said delivering means including passage means communicating between said test fluid chamber and said specimen chamber, and a deformable wall portion on said housing for manual deformation to deliver said test fluid from said test fluid chamber through sid passage means to said specimen chamber; and said housing further defining an outlet port leading from said specimen chamber to the exterior of said housing, and means for closing said outlet port during contact of the specimen with sid test fluid within said specimen chamber, said deformable wall portion being manually deformable for transferring at least a portion of the collected specimen and the test fluid contacted therewith from said specimen chamber through said outlet port to the exterior of said housing.

31. The specimen test unit of claim 30 wherein said means for closing said outlet port comprises a removable cap.

32. The specimen test unit of claim 30 wherein said collecting means comprises a swab.

33. The specimen test unit of claim 30 wherein said means for closing said outlet port comprises a filter.

34. The specimen test unit of claim 33 wherein said filter has at least one reagent carried thereby.

35. The specimen test unit of claim 33 wherein said filter comprises at least two filter members disposed for series passage of said portion of the collected specimen and the test fluid contacted therewith, at least one of said filter members being formed from a hydrophobic material.

36. A specimen test unit for use in collection and analysis of a biological specimen, said test unit comprising:

a housing defining a specimen chamber with at least one test fluid therein;

specimen collecting means for collecting the specimen and for delivering the collected specimen into the specimen chamber for contacting the collected specimen with the test fluid;

said housing defining an outlet port leading from said specimen chamber to the exterior of said housing;

means for occluding said outlet port to fluid flow during contact of the specimen with said at least one test fluid, said occluding means having passage means formed therein for communicating said specimen chamber with the exterior of said housing, said passage means having a sufficiently small size to prevent unforced flow of said specimen and test fluid therethrough; and means for delivering the specimen and a portion of said test fluid through said passage means to the exterior of said housing for further analysis, said delivering means comprising means for pressure forced flow of the specimen and said test fluid through said passage means wherein said means for pressure forced flow of the specimen and said test fluid through said passage means comprises a deformable wall portion of said housing for manual deformation to increase the relative pressure within said specimen chamber and thereby pressure force the specimen and said test fluid to flow through said passage means.

* * * * *